United States Patent
Scott et al.

(10) Patent No.: US 7,045,184 B2
(45) Date of Patent: *May 16, 2006

(54) POLYVINYL ALCOHOL COMPOSITIONS

(75) Inventors: Robert A. Scott, Sint Niklaas (BE); Dominque Cadé, Colmar (FR); Xiongwei He, Andolsheim (FR)

(73) Assignee: Warner-Lambert Company, Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/840,257

(22) Filed: Apr. 23, 2001

(65) Prior Publication Data

US 2001/0043999 A1 Nov. 22, 2001

Related U.S. Application Data

(63) Continuation of application No. 09/221,139, filed on Dec. 24, 1998, now abandoned.

(30) Foreign Application Priority Data

Mar. 11, 1998 (FR) ................................... 98 02983

(51) Int. Cl.
*A61K 9/48* (2006.01)
(52) U.S. Cl. ..................... 428/35.7; 424/454; 424/463; 424/486; 53/454; 206/528
(58) Field of Classification Search ........ 424/451–456, 424/461–463, 474, 486; 53/454, 900; 206/528, 206/530; 428/35.7
See application file for complete search history.

(56) References Cited

U.S. PATENT DOCUMENTS

| | | | |
|---|---|---|---|
| 3,015,128 A | 1/1962 | Somerville | 18/2.6 |
| 3,629,140 A * | 12/1971 | Bayless et al. | 252/316 |
| 3,664,963 A * | 5/1972 | Pasin | 427/213.36 |
| 4,244,836 A * | 1/1981 | Frensch et al. | 252/316 |
| 4,349,563 A | 9/1982 | Gilbert et al. | 424/274 |
| 4,627,850 A * | 12/1986 | Deters et al. | 604/892 |
| 5,264,223 A | 11/1993 | Yamamoto et al. | 424/451 |
| 5,434,069 A | 7/1995 | Tsaur et al. | 435/188 |
| 5,614,217 A | 3/1997 | Chiprich et al. | 424/451 |
| 5,885,617 A | 3/1999 | Jordan | 424/474 |
| 6,517,865 B1 * | 2/2003 | Cade et al. | 424/451 |
| 6,770,294 B1 * | 8/2004 | Scott et al. | 424/456 |

FOREIGN PATENT DOCUMENTS

| | | | |
|---|---|---|---|
| GB | 2 006011 A * | 5/1979 | |
| WO | WO 9704755 | 2/1997 | |

* cited by examiner

*Primary Examiner*—Harold Pyon
*Assistant Examiner*—Sow-Fun Hon
(74) *Attorney, Agent, or Firm*—Rosemary M. Miano; Evan J. Federman

(57) ABSTRACT

The invention concerns polyvinyl alcohol (PVA) compositions for the use in pharmaceutical, veterinary, food, cosmetic or other products like films for wrapping food, aspics or jellies, preferably for predosed formulations like soft or hard capsules. Compared with hard gelatine capsules (HGC) capsule films consisting of PVA have extremely low water vapour permeability and much lower water content.

3 Claims, 2 Drawing Sheets

POLYVINYL ALCOHOL COMPOSITIONS

"This application is a continuation of application Ser. No. 09/221,139 filed on Dec. 24, 1998, now abandoned which claims priority to French Application Ser. No. 98/02983 filed on Mar. 11, 1998."

FIELD OF THE INVENTION

The invention concerns polyvinyl alcohol (PVA) compositions for the use in pharmaceutical, veterinary, food, cosmetic or other products like films for wrapping food, aspics or jellies, preferably for predosed formulations like soft or hard capsules. Compared with hard gelatine capsules (HGC) capsule films consisting of PVA have extremely low water vapour permeability and much lower water content.

A second embodiment of the invention is the use of the film composition for the manufacturing of hard capsules by conventional dip moulding processes as normally used in the production of conventional hard gelatin capsules.

BACKGROUND OF THE INVENTION

For the industrial manufacturing of pharmaceutical capsules gelatine is most preferred for its gelling, film forming and surface active properties. The manufacture of hard gelatin capsules by dip moulding process exploits fully its gelling and film forming abilities. Such capsules are manufactured by dipping mould pins into a hot solution of gelatin, removing the pins from the gelatin solution, allowing the gelatin solution attached on pins to set by cooling, drying and stripping the so-formed shells from the pins. The setting of the solution on the mould pins after dipping is the critical step to obtain an uniform thickness of the capsule shell.

A main limitation of the use of hard gelatine capsules results from an exchange of moisture between capsules and fills. Gelatine naturally has hygroscopic properties and hard gelatine capsules generally contain about 10 to 16% by weight of water. This water content is a function of the relative humidity (RH) of the surroundings. When capsules are filled and stored in a vapour tight container, the moisture will redistribute between the various components until an uniform relative humidity is attained in the vapor phase of capsule shell, fill and surrounding.

A further disadvantage of the gelatin film and an unwanted limitation of its use is its high water vapour permeability, which results in a high rate of water vapour transport through the gelatine shell of capsules with a hygroscopic fill or of capsules stored in a humid environment. Results of experimental tests show that at 22° C. by a difference of 50% in the RH between both sides of a 100 µm gelatine film during a period of 24 hours an amount of twice the gelatin film weight of water vapour is permeated through the film. Consequently, when capsules exposed to an open environment, the fill will take up moisture from the environment by permeation through the capsule shell until equilibrium is achieved.

Moisture take-up of the fill of a capsule by moisture exchange with or permeation through the capsule shell may adversely affect the properties of the fill: powder fills may agglomerate or, more seriously, fills may undergo chemical degradation e.g. by hydrolysis. Generally pharmaceutical gelatin capsules therefore are to be stored a dry environment.

The affinity of capsules and their fills and the moisture exchange between capsules and fills can be determined by the sorption-desorption isotherms for the materials of capsules and fills. For gelatine this is well described in the literature, e.g. in K. Ito & al., Chem. Pharm. Bull. 17 (3) 1969, 1134–37. M. J. Kontny & al., Int. J. Pharm. 54, 1989, 79–85 describe a mathematical model to predict the final relative water vapor pressure in a closed system for a multicomponent mixture of solids knowing the initial water content for each component. From the final relative pressure and individual sorption-desorption isotherms, it is then possible to estimate the extent to which mixt. redistributes via the vapor phase among the various components.

Only few published studies are related to the permeability of hard gelatine capsules for water vapour. W. A. Strickland & al., J. Pharm. Sci., 51 (10) 1962, 1002–5 describes the water vapor diffusion through hard gelatin capsules and concludes that gelatine capsules offer little protection to a hygroscopic fill from atmospheric water vapour. To overcome this drawback in WO 97/04755 it has been suggested to incorporate polyol additives into the composition of the gelatin film of hard gelatin capsules.

It is well known that PVA film compositions have extremely low water vapour permeability, the lowest among known hydrosoluble film forming materials, and it is widely used for coating compositions, especially for pharmaceutical formulations like tablets as described in WO 96/01874.

EP-A-0 180 287 teaches the use of PVA in combination with cellulose ethers in hard capsule film compositions. In this compositions, the setting of the dipping solution is achieved by thermal gelation of a cellulose ether like Hydroxypropylmethyl cellulose (HPMC). However, to obtain acceptable setting properties of the film forming composition, the HPMC content must be very high, even higher than the PVA content. Consequently the benefits of the properties of PVA will significantly be reduced in such compositions.

The problem of the invention is therefore the provision of polyvinyl alcohol (PVA) compositions for the use in pharmaceutical, veterinary, food, cosmetic or other products like films for wrapping food, aspics or jellies, preferably for predosed formulations like soft or hard capsules and wherein the PVA composition has in aqueous solution sufficient setting ability.

SUMMARY OF THE INVENTION

Surprisingly it has been found that the addition of a very small amount of a setting system, preferably containing hydrocolloids, most preferably polysaccharides, improves drastically the setting ability of PVA solutions for the production of hard PVA capsules by conventional dip moulding processes.

Object of the invention is therefore the provision of PVA/setting system compositions, preferably for films for pharmaceutical, veterinary, food, cosmetic or other products, especially preferred for the production of capsules for predosed forms, especially hard capsules.

BRIEF DESCRIPTION OF THE DRAWINGS

The following drawings are illustrative of embodiments of the invention and are not intended to limit the invention as encompassed by the claims forming part of the application.

DETAILED DESCRIPTION OF THE INVENTION

Figure 1:
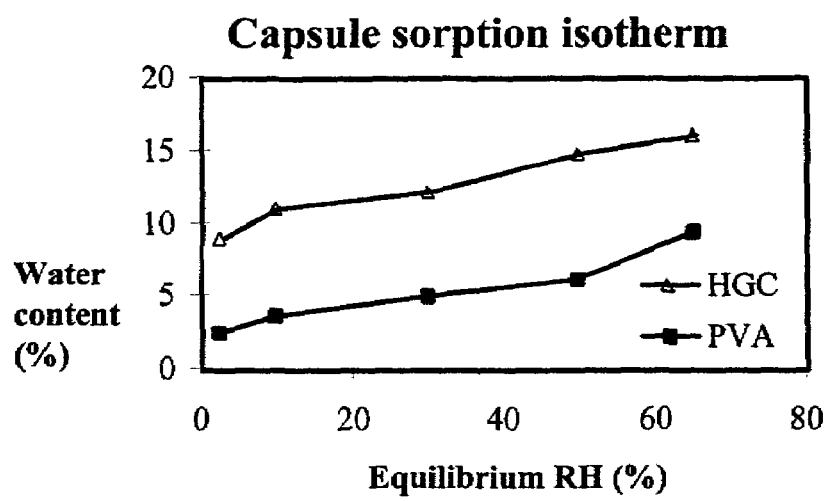
FIG. 1 is a graph showing a comparison of the sorption isotherm of capsules prepared in accordance with the present invention and conventional hard gelatin capsules.

The addition of a setting system, preferably based on polysaccharides, to PVA solutions enables the adaptation of specific and desired gelling properties for the production of hard PVA capsules by conventional dipping processes. For the production of such capsules it is extremely important that the film forming PVA solution remaining on the mould pins after dipping is prohibited from flowing down the pins. Otherwise the obtained film will not have the desired uniform thickness.

Consequently hard PVA capsules can be produced with the same equipment used for the production of conventional hard gelatine capsules in the range of same process conditions. Furthermore capsules produced from compositions of the instant invention have the same dimensional specifications and allow the use of the existing filling machinery and do not require specific and new equipment for the filling process.

The PVA capsules produced from the film forming compositions of the invention are consisting mainly of PVA and have consequently the properties of pure PVA such as extremely low water vapour permeability, low hygroscopicity, excellent piercing behaviour under low relative humidity, and in addition the advantages of gelatin capsules as examplified.

The PVA concentration in the dipping solution is in a range of 10 to 60%, preferably in the range of 20 to 40% by weight.

The setting system includes a hydrocolloid or mixtures of hydrocolloids and may contain in addition cations and/or sequestering agents.

Suitable hydrocolloids or mixtures producing synergistic properties may be selected from natural seaweeds, natural seed gums, natural plant exudates, natural fruit extracts, bio-synthetic gums, gelatins, bio-synthetic processed starch or cellulosic materials, preferred are the polysaccharides.

The preferred polysaccharides are alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, and other exocellular polysaccharides. Preferred are exocellular polysaccharides.

The preferred exocellular polysaccharides are xanthan, acetan, gellan, welan, rhamsan, furcelleran, succinoglycan, scleroglycan, schizophyllan, tamarind gum, curdlan, pullulan, dextran.

The preferred hydrocolloids are kappa-carrageenan or gellan gum or combinations like xanthan with locust bean gum or xanthan with konjac mannan.

Among the setting systems mentioned above, the systems of kappa-carrageenan with cation and gellan gum with cation are specifically preferred. They produce high gel strength at low concentrations and have excellent compatibility with PVA.

The amount of the hydrocolloid is preferably in the range of 0.01 to 5% by weight and especially preferred 0.03 to 1.0% in the aqueous PVA solution.

The cations are preferably selected from $K^+$, $Na^+$, $Li^+$, $NH_4^+$, $Ca^{++}$ or $Mg^{++}$, for kappa-carrageenan are preferred $K^+$, $NH_4^+$ or $Ca^{++}$. The amount of cations is preferably 0.001 to 3%, especially 0.01 to 1% by weight in the aqueous PVA solution.

The preferred sequestering agents are ethylenediaminetetraacetic acid, acetic acid, boric acid, citric acid, edetic acid, gluconic acid, lactic acid, phosphoric acid, tartaric acid or salts thereof, methaphosphates, dihydroxyethylglycine, lecithin or beta cyclodextrin and combinations thereof. Especially preferred is ethylenediaminetetraacetic acid or salts thereof or citric acid or salts thereof. The amount is preferably 0.001 to 3%, especially 0.01 to 1% by weight of the dipping solution.

In addition, it is possible to incorporate a small quantity of an anti-foaming agent into the PVA solution to avoid the forming of bubbles which may lead to visuable defects on the capsules.

The PVA capsules produced from the solutions as described will consequently contain by weight of 2 to 7% of water, 90 to 97% of PVA, 0.01 to 10%, preferably 0.05 to 5% of hydrocolloids, 0.001 to 5%, preferably 0.01 to 3% of cations depending on the hydrocolloids used, and optionally 0.001 to 5%, preferably 0.01 to 3% of sequestering agents.

The inventive PVA compositions may contain in a further aspect additional pharmaceutically or food acceptable colouring agents in the range of from 0 to 10% based upon the weight of the PVA. The colouring agents may be selected from azo-, quinophthalone-, triphenylmethane-, xanthene- or indigoid dyes, iron oxides or hydroxides, titanium dioxide or natural dyes or mixtures thereof. Examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

The PVA capsules of the invention may be coated with a suitable coating agent like cellulose acetate phthalate, polyvinyl acetate phthalate, methacrylic acid gelatines, hypromellose phthalate, hydroxypropylmethyl cellulose phthalate, hydroxyalkyl methyl cellulose phthalates or mixtures thereof to provide e.g. enteric properties.

The PVA capsules of the invention may be used for the production of containers for providing unit dosage forms for example for agrochemicals, seeds, herbs, foodstuffs, dyestuffs, pharmaceuticals, flavouring agents and the like.

The inventive gelatin composition makes it useful for the encapsulation of caplets in a capsule, especially in a tamperproof form. The encapsulation of a caplet in a capsule is preferred processed by cold shrinking together capsule parts, which are filled with a caplet, which comprises the steps providing empty capsule parts, filling at least one of said capsule parts with one or more caplets, putting said capsule parts together, and treating the combined capsule parts by cold shrinking.

The inventive PVA capsules are also useful for encapsulating and sealing the two capsule halves in a process in which one or more layers of a banding agent are applied over the seam of the cap and body, or by a liquid fusion process wherein the filled capsules are wetted with a hydroalcoholic solution that penetrates into the space where the cap overlaps the body, and then dried.

Capsules or films with the inventive PVA composition may be manufactured with conventional machines by the conventional processes like extrusion moulding, injection moulding, casting or dip moulding.

The PVA capsule production and properties are demonstrated by the following examples and tests:

EXAMPLE 1

Hard PVA Capsule Production

To 3.50 kg of deionised water is added 5 g of potassium acetate (0.10% by weight in the solution), followed by addition of 10 g kappa-carrageenan (0.20% by weight) and 2 g of Montane 80 (as anti-foaming agent, 0.04%) under stirring at about 70° C. When kappa-carrageenan is dissolved, 1.35 kg (27% by weight) of PVA (which has a viscosity of 5 cps for a 4% aqueous solution at 20° C.) is added at 60° C. under slow stirring until the PVA is completely dissolved and the solution is defoamed.

The PVA solution thus prepared is then poured into a dipping dish of a pilot machine of conventional hard gelatine capsule production equipment. While keeping the temperature of dipping PVA solution at about 60° C., natural transparent hard PVA capsules of size 0 and size 3 were produced according to the conventional process with the same dimensional specifications to the conventional hard gelatine capsules. Expectable from the extremely low water vapour permeability of PVA, the drying time of capsules is rather long.

EXAMPLE 2

Water Vapor Sorption of Hard PVA Capsules

The sorption isotherm of PVA capsules according to example 1 has been investigated and compared with the isotherm of hard gelatin capsules. The experiments demonstrate that PVA capsules have much lower hygroscopicity than HGC.

The results are shown in FIG. 1.

EXAMPLE 3

Moisture Take-up of Hard Capsule Fills

The moisture take-up of fills encapsulated in PVA capsules or HGC has been investigated. The capsules were equilibrated at 22° C. and 50% RH, then filled with dried polyvidone or dried maize starch. After closing, the capsules were stored at 22° C. and 50% RH. The moisture take-up by the capsule fills have been determined by the increase of the weight of the filled capsule. The experiments demonstrate that PVA capsules have extremely low water vapour permeability.

Figure 2:
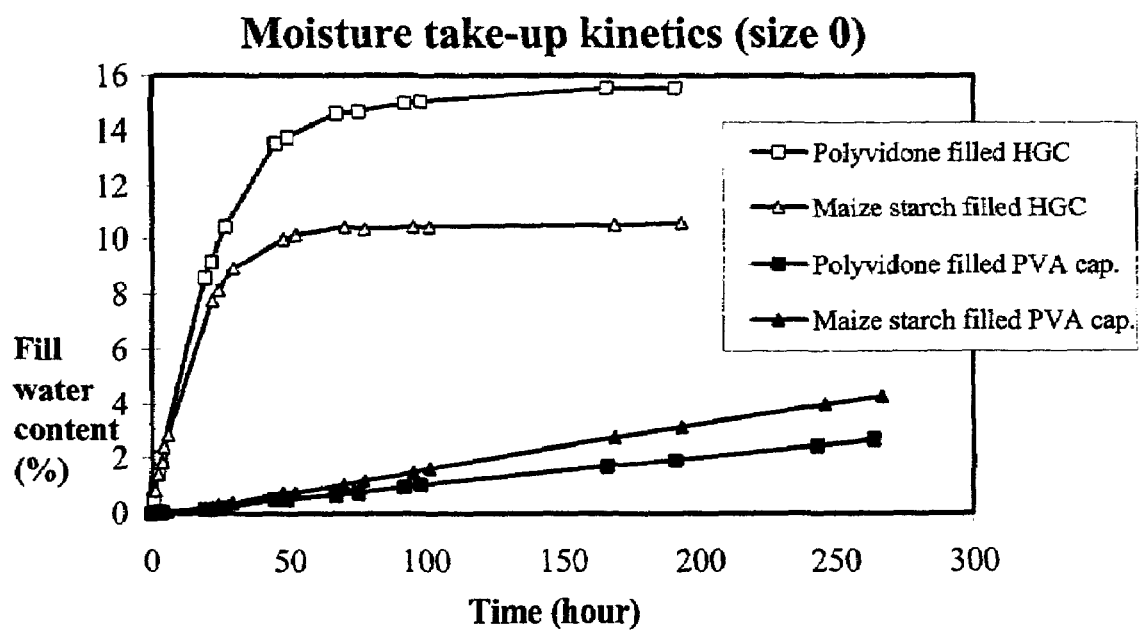
FIG. 2 is a graph showing a comparison of the moisture take-up of ills encapsulated in capsules of the present invention as compared to conventional hard gelatin capsules.

The kinetics of moisture take-up are shown in FIG. 2.

Table 1 shows the proportion of the permeabilities of PVA capsules and hard gelatin capsules:

TABLE 1

| Fill | Polyvidone | Maize starch |
|---|---|---|
| Permeability (PVA cap.) Permeability (HGC) | 0.017 | 0.027 |

EXAMPLE 4

Piercing Behaviour

Under B.I.L. inhalator test conditions, capsules of size 0 have been pierced and their behaviour examined. PVA capsules did not show any breaking or cracking in contrary to hard geletin capsules and have therefore excellent piercing behaviour even at low RH.

The test results are shown in Table 2:

| Equilibrium RH (%) | 50 | 10 | 2.5 |
|---|---|---|---|
| HGC broken (%) | 0 | 30 | 100 |
| PVA cap. broken (%) | 0 | 0 | 0 |

EXAMPLE 5

Dissolution Test

Under USP XXIII dissolution test conditions the behavior of PVA capsules size 0 and 3 filled with acetaminophen has been tested in deionised water at 37° C. PVA capsules have good dissolution properties.

Figure 3:
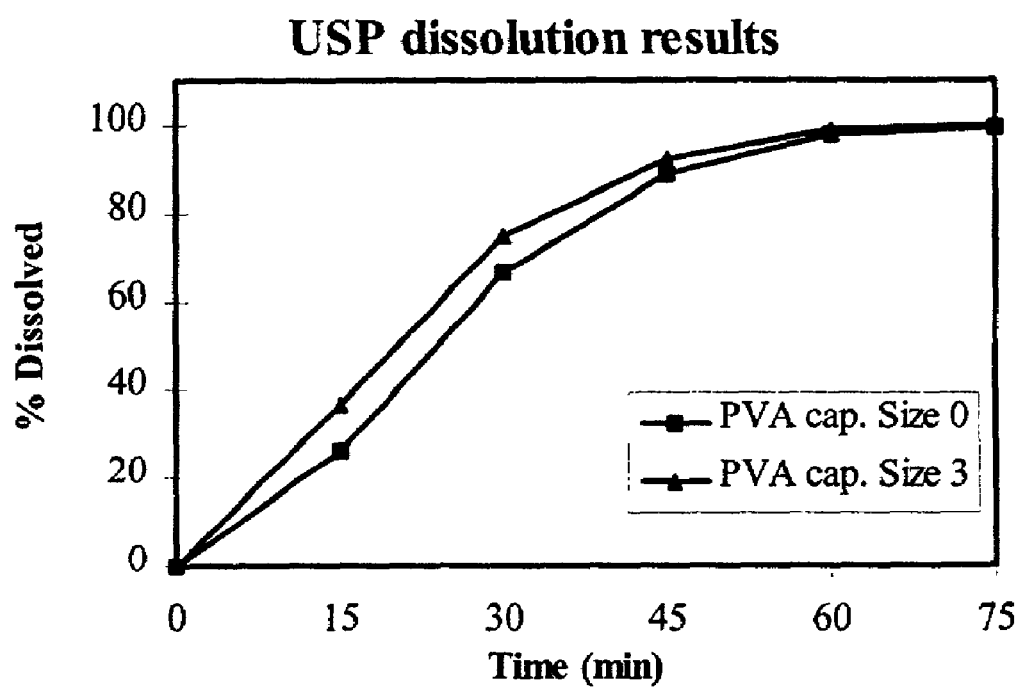
FIG. 3 is a graph showing the dissolution results under USP XXIII dissolution test conditions for the capsules prepared in accordance with the present invention.

The results of the dissolution tests are shown in FIG. 3.

The invention claimed is:

1. A capsule comprising 90–97% by weight of polyvinyl alcohol, 2 to 7% by weight water; a setting system comprising 0.01 to 10% by weight of a hydrocolloid or mixtures thereof; 0.001 to 5% by weight of cations based on the total weight of the capsule; and a sequestering agent selected from the group consisting of ethylenediaminetetraacetic acid, acetic acid, boric acid, citric acid, edetic acid, gluconic acid, lactic acid, phosphoric acid, tartaric acid or salts thereof, metaphosphates, dihydroxyethylglycine, lecithin, beta cyclodextrin and combinations thereof; wherein the capsule has at least one coating thereon made from a substance selected from the group consisting of cellulose acetate phthalate, polyvinyl acetate phthalate, methacrylic acid gelatins, hypromellose phthalate, hydroxypropyl methyl cellulose phthalates, hydroxyalkyl methyl cellulose phthalates and combinations thereof; and has two halves sealed together by a liquid fusion process.

2. The capsule according to claim 1, wherein the amount of the sequestering agent is 0.001 to 5% by weight based on the total weight of the composition.

3. The capsule according to claim 2, wherein the sequestering agent is selected from the group consisting of ethylenediaminetetraacetic acid, citric acid, their respective salts and combinations thereof.

* * * * *